United States Patent
Tipler et al.

[11] Patent Number: 5,958,246
[45] Date of Patent: Sep. 28, 1999

[54] STANDARDIZATION OF CHROMATOGRAPHIC SYSTEMS

[75] Inventors: Andrew Tipler, Trumbull; Adam J. Patkin, Hamden; Andrew P. Bajorinas, Stamford; Jerry E. Cahill, Trumbull, all of Conn.; Ralph L. Carter, Thame, United Kingdom

[73] Assignee: The Perkin-Elmer Corporation, Norwalk, Conn.

[21] Appl. No.: 09/079,080

[22] Filed: May 14, 1998

Related U.S. Application Data

[60] Provisional application No. 60/046,671, May 16, 1997.

[51] Int. Cl.[6] .................................................. B01D 15/08
[52] U.S. Cl. ................................... 210/656; 95/82; 95/87
[58] Field of Search ..................................... 95/82, 83, 84, 95/85, 86, 87, 88, 89; 96/101, 102, 103; 210/656

[56] References Cited

U.S. PATENT DOCUMENTS

| | | | |
|---|---|---|---|
| 4,579,663 | 4/1986 | Poile | 210/656 |
| 5,303,165 | 4/1994 | Ganz | 364/571.01 |
| 5,405,432 | 4/1995 | Snyder | 95/82 |
| 5,545,252 | 8/1996 | Hinshaw | 95/82 |
| 5,711,786 | 1/1998 | Hinshaw | 95/82 |

*Primary Examiner*—Ernest G. Therkorn
*Attorney, Agent, or Firm*—David Aker; Herbert S. Ingham

[57] ABSTRACT

A primary chromatographic system is operated with a standard sample at several temperatures to generate primary retention times which are fitted to a function to determine thermodynamic constants to relate the times to temperature. A target chromatographic system is operated with the standard sample to generate secondary retention times. The function is used with these times to determine and an effective column parameter for the target system. The function then is used with this parameter and the primary times to determine a pressure program. Further operation of the target system with a application sample and the pressure program effects standardized retention times. A particular searching technique is utilized to apply the function. A temperature calibration technique with a selected sample measures column temperature for the target system, and a validation is done on the target system.

52 Claims, 8 Drawing Sheets

STANDARDIZATION OF CHROMATOGRAPHIC SYSTEMS

This application claims the benefit of Provisional Patent Application Ser. No. 60/046,671 filed on May 16, 1997.

This invention relates to chromatographic systems and particularly to the standardization of such systems.

BACKGROUND

Chromatography involves physically separating constituents of a sample in a carrier fluid and measuring the separation. In gas chromatography (GC) the carrier is a gas or at least a supercritical fluid which acts similarly in the system. In liquid chromatography (LC) the carrier is a liquid. In either case a pulse of the sample is injected into a steady flow of the carrier, and the constituents are adsorbed or absorbed and desorbed by a stationary phase material in a column. At the end of the column the individual components are more or less separated in time. Monitoring the column effluent with a suitable detector provides a pattern of retention times which, by calibration or comparison with known samples, indicates the constituents of the sample qualitatively and quantitatively. The main components of such a system are the column, an injector with a mixing chamber for introducing the sample into the carrier, a detector at the outlet end of the column, fluid controls, and a computer for processing and displaying the output of the detector. The display is generally in the form of retention times. In GC an oven generally is used to elevate temperature to maintain the sample in a volatile state, and to improve the discrimination of constituents. Various gas chromatographic systems are disclosed in U.S. Pat. Nos. 5,405,432, 5,545,252 ("Hinshaw 1"), U.S. patent application Ser. No. 08/734,689 filed Oct. 21, 1996 ("Hinshaw 2"), and an article "The Effects of Inlet Liner Configuration and Septum Purge Flow Rate on Discrimination in Splitless Injection" by J. V. Hinshaw, J. High Resolution Chromatography 16, 247–253 (Apr. 1993). A liquid chromatographic system is disclosed in U.S. Pat. No. 4,579,663.

Interpretations of retention time patterns in chromatography tend to require skill and experience, as different systems and particularly different columns behave differently so as to effect different patterns for the same sample material. An operator selects operating parameters, such as temperature and pressure, or may vary these parameters during a run, according to judgment. Thus uses of these systems for evaluating samples is dependent on the skills of the operators, and it has been difficult to compare results of different systems, columns and operators.

When a chromatographic method is developed it is often desirable to transfer it to the same system at a later time, the same system with a different column, or another system. The task is made more complicated by other factors including different calibrations of temperatures and pressures, and different oven geometries resulting in different temperature gradients. Differing characteristics of columns include length, internal diameter, phase thickness and phase chemistry, and these characteristics are difficult to determine with precision without destroying the column. These variations in systems, particularly columns, cause the retention times to change for different systems and the same system at different times, even switching the order of some peaks. Recalibration is complex and can be time consuming. Standardization would be desirable, such as is done in optical spectroscopy, for example as disclosed in U.S. Pat. No. 5,303,165 (Ganz et al.) It would be particularly desirable to be able to provide a useful library of basic standards associated with specified types of columns, so that chromatographic results may be compared universally.

Objects of the invention are to provide a novel method and a novel means for standardizing chromatographic systems so as to allow direct comparison of information generated from different systems and the same system at different times, including different chromatographic columns and the same column at different times. Particular objects are to provide a novel method and a novel means for establishing certain operating parameters for each chromatographic system such that retention times are substantially identical for different systems and the same system at different times. Other objects are to provide a novel method and a novel means for optimizing parameters for chromatographic systems. Additional objects are to provide a novel method and a novel means for measuring temperature of chromatographic columns, particularly to further standardization, and also to provide a novel method and a novel means for validating chromatographic systems.

SUMMARY OF THE INVENTION

The foregoing and other objects are achieved, at least in part, by a method and a means for standardizing a target chromatographic system with a primary chromatographic system. Each system includes carrier means for passing a fluid carrier through the column, injection means for injecting a pulse of sample into the carrier to effect a mixture passing through the column subject to characteristic retention times for constituents of the sample, detector means receptive of the mixture for effecting signals representative of the retention times, and processing means receptive of the signals for presenting corresponding retention indicators. Each system has system parameters and operating parameters, the operating parameters comprising a first parameter having selectable first programming and a second parameter having selectable second programming, each programming being with respect to time. The retention times are related to the system parameters and the operating parameters by a mathematical function having function parameters including thermodynamic constants associated with interactions of the constituents with the column.

In preferred embodiments, the system is a gas chromatographic system with a gas carrier, the first parameter is column temperature and the second parameter is inlet pressure of the carrier to the column. Also, preferably, the retention indicators are retention times, and the system parameters include column dimensions.

The primary system is operated with a standard sample, a selected primary second program (e.g. pressure) for the second parameter, and a plurality of selected primary first programs (e.g. temperature) for the first parameter, so as to generate corresponding primary retention indicators (e.g. times). The primary retention indicators and the first programs are fitted to the function, with the second program, so as to determine thermodynamic constants whereby the function is representative of a virtual chromatographic system. The thermodynamic constants are stored for future application with the target chromatographic system.

A target chromatographic system is initially operated with the standard sample, substantially the primary second program, and a plurality of secondary first programs, so as to generate corresponding secondary retention indicators. Effective system parameters (e.g. column dimensions) are established for the target chromatographic system, by assumption, earlier measurement or a technique according to an aspect of the invention (explained below). A secondary second program then is determined for which, with the effective system parameters, the function yields substantially the primary retention indicators for the primary first programs.

In an actual operation, the target chromatographic system is operated with a application sample, the secondary second program and a selected first program, so as to generate at least one corresponding test retention indicator. By use of such secondary program, each test retention indicator is standardized to the virtual chromatographic system.

The function relating retention times to the parameters such as temperature and pressure are based preferably on theoretical relationships of a chromatographic system. As such a function generally is complex, special techniques may be required for its application, particularly in the determination of an effective column dimension and a secondary second (pressure) program. In an aspect of the invention, a method and a means are provided for determining values for one or more specified parameters for a chromatographic system. There are system parameters (e.g. column dimensions) and operating parameters (e.g. temperature and pressure) related to retention times by a mathematical function having function parameters including these parameters as well as others such as thermodynamic constants related to interactions of the sample with a stationary phase in the column. The function parameters have predetermined or assumed values except for the specified parameters. A specified parameter may be column inlet pressure, or column length.

The system (e.g. target system) is operated so as to generate retention indicators. An initial data base is provided, defining ranges of potential values of the specified parameter or parameters. Theoretical retention indicators are computed with the function for the potential values and the predetermined or assumed values, differences are computed between the theoretical retention indicators and the secondary retention indicators, and the differences are searched for a minimum therein, such that the minimum establishes an effective value for each specified parameter.

In another aspect a method and a means are provided to determine column temperature of the target chromatographic system relative to that of the primary chromatographic system. A temperature standard is provided comprising a calibration compound having temperature dependent retention time, and a plurality of homolog standards having a homolog relationship between corresponding retention indicators and retention times. The primary chromatographic system is operated with the temperature standard, a selected primary pressure program and a plurality of selected calibration temperatures so as to generate a primary set of retention times for each calibration temperature, each primary set comprising homolog retention times for the homolog standards and a compound retention time for the calibration compound. The homolog relationship and the primary set of retention times are first utilized for each calibration temperature to determine calibration constants for a temperature relationship relating retention indicator for the calibration compound to column temperature for the primary system. The target chromatographic system is operated with the temperature standard and a measured column temperature so as to generate a test set of retention times, the test set comprising test retention times for the homolog standards, and a test retention time for the calibration compound. The homolog relationship and the test set of retention times are secondly utilized to determine a secondary retention indicator for the calibration compound. The temperature relationship is applied with the calibration constants and the secondary retention indicator to determine a calibrated temperature corresponding to the measured temperature.

In a further aspect a method and a means are provided for validating a target gas chromatographic system having a calibrated temperature relationship between its column temperature and the column temperature for a primary gas chromatographic system. A validation standard is provided comprising selected validation constituents and a plurality of homolog standards having a homolog relationship between corresponding retention indicators and retention times. The primary chromatographic system is operated with the validation standard, a selected primary pressure program, and a primary validation temperature for the column, so as to generate primary validation retention times for the validation constituents and homolog retention times for the homolog standards. The target chromatographic system is operated with the validation standard, substantially the primary pressure program, and the measured column temperature so as to generate secondary validation retention times for the validation constituents and test retention times for the homolog standards. The homolog retention times are utilized to determine primary homolog parameters for the homolog relationship, and the test retention times are utilized to determine secondary homolog parameters for the homolog relationship. The homolog relationship, the primary homolog parameters and the primary validation retention times are utilized to effect preliminary retention indicators. The homolog relationship, the secondary homolog parameters and the secondary validation retention times are utilized to effect secondary validation retention indicators. The preliminary retention indicators are adjusted with the temperature relationship to a calibrated temperature corresponding to the secondary validation temperature so as to effect primary validation retention indicators. Differences between corresponding primary validation retention indicators and secondary validation retention indicators are calculated, and it is determined whether the differences are less than a predetermined limit corresponding to whether the target chromatographic system is valid.

DETAILED DESCRIPTION

The invention is utilized in an otherwise conventional or other desired gas chromatographic (GC) system such as described in the aforementioned U.S. Pat. No. 5,545,252 ("Hinshaw 1") and U.S. patent application Ser. No. 08/734,689 ("Hinshaw 2"), each being of the present assignee and incorporated herein in its entirety by reference. A suitable system is a Perkin-Elmer Autosystem XL (trademark).

Figure 1:
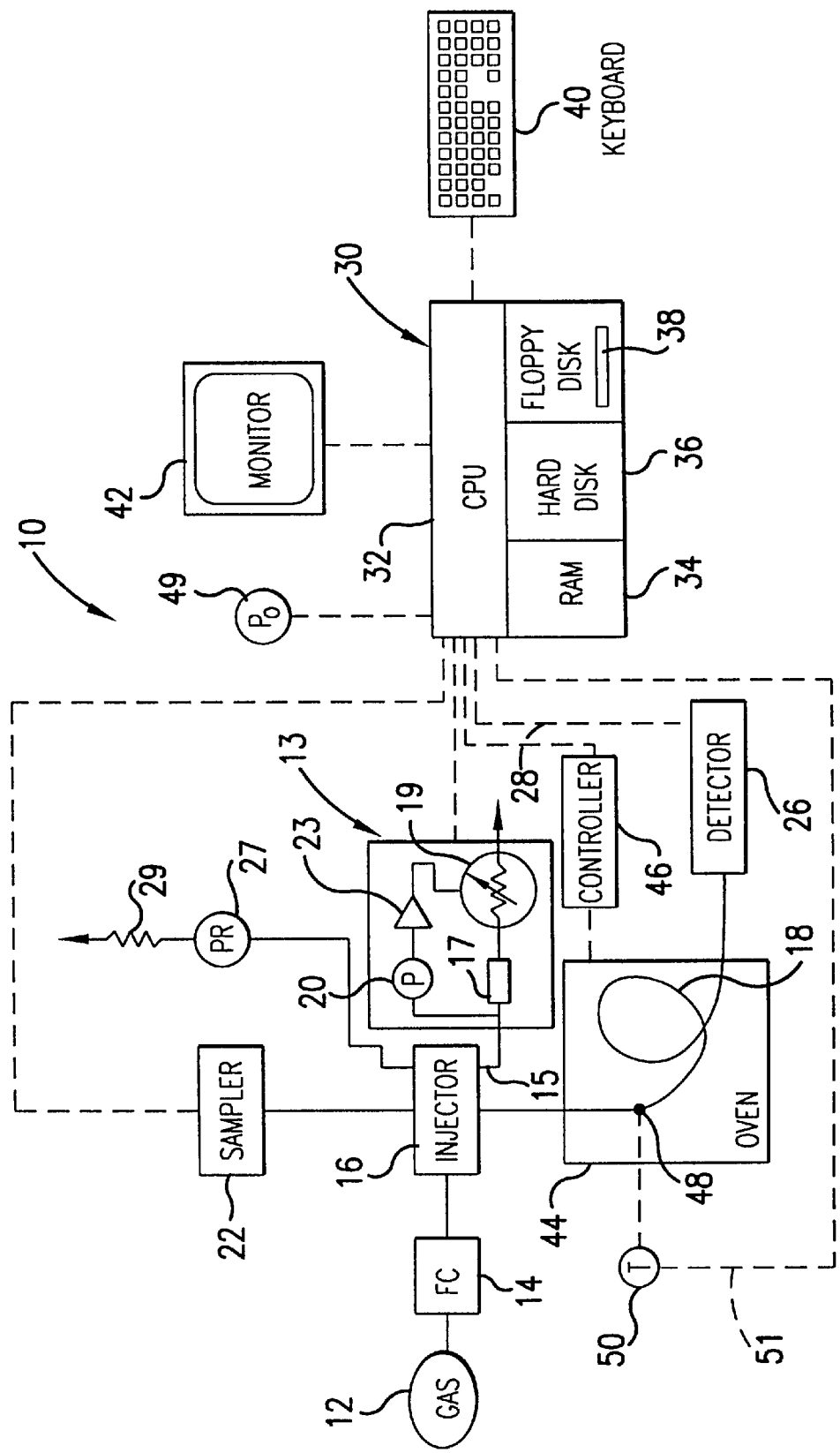
FIG. 1 is a schematic drawing of a chromatographic system incorporating the invention.
Figure 2:
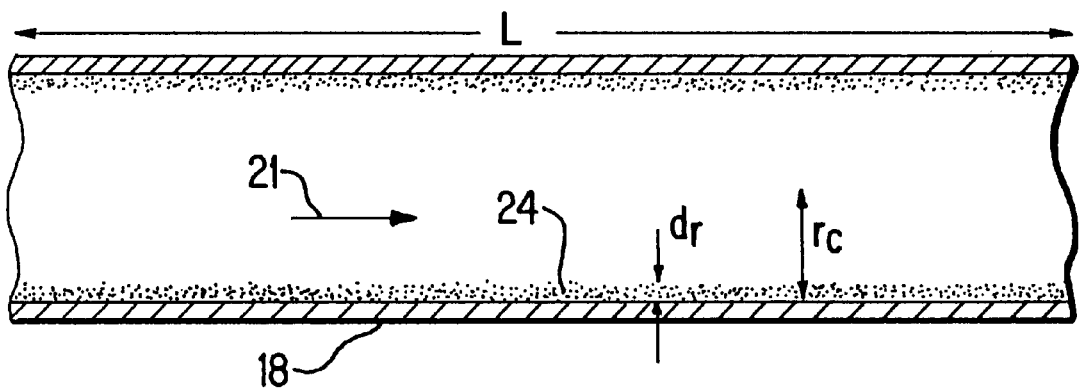
FIG. 2 is a longitudinal section of a portion of a chromatographic column used in the system of FIG. 1.

A preferred type of GC system 10 (FIG. 1) utilizes split flow with back pressure regulation in the manner illustrated in the aforementioned Hinshaw article, FIG. 2(b) thereof. A carrier gas from a pressure-regulated source 12 is supplied through a gas flow controller 14 to an injector device 16, each of which may be essentially any conventional or other desired type. For example, the flow controller is of the type taught in Hinshaw 2, and the injector is of the type taught in Hinshaw 1. A portion of the carrier is passed from the injector 16 into and through a chromatographic column 18 formed of a long tube, e.g a fused silica tube 25 m long and 0.25 mm inside diameter, having a selected stationary phase on the inside column wall such as methyl silicone 0.25 $\mu$m thick.

Most of the remainder of the inlet flow passes out to the ambient space (normally atmosphere) through a back pressure regulator 13, for example as taught in Hinshaw 2, so as to maintain a constant, selected pressure of carrier into the column passage. The back pressure regulator is connected to a split flow outlet 15 from the injector, preferably with a charcoal filter 17 in the line to protect a downstream component from clogging. In one form of pressure controller, a variable flow restrictor 19 follows the filter. A pressure transducer 20 is connected to measure pressure at the split flow outlet which is the pressure at the inlet to the column. An electronic feedback device 23 connected from the transducer to the restrictor is utilized, preferably under control by computer 30. A conventional purge gas outlet from the injector comprises, for example, a fixed pressure regulator 27 tapped into the injector and connected to a fixed gas flow resistor 29.

A sample material is formed of chemical constituents, generally organic molecules including those containing other elements besides carbon and hydrogen, such as chlorine, oxygen, nitrogen and/or sulphur. A pulse of the sample is injected from a sample source into the carrier in the injector device where a mixture is formed with the carrier gas. The pulsed mixture passes through the column during a time period which typically is several minutes after the sample injection. In the column 18 (FIG. 2) a stationary phase of a suitable substance on the tube wall adsorbs from the carrier gas 21 and then desorbs the chemical constituents of the sample.

Different constituents have different affinities for the stationary phase and thereby exit the column at different characteristic times, known as retention times, associated with different times for retention in the stationary phase. The velocity of the carrier gas ("mobile phase") contributes to the total retention time; the term "retention time" means the total time from injector to detector in the stationary and mobile phases. A detector 26 at the column outlet measures a physical property of the carrier and mixture, the magnitude of the property changing with each constituent passing through. Various types of detectors are used, such as hot wire, flame ionization, electron capture, thermionic and flame photometric. The detector effects signals on a line 28, the signals being representative of the retention times as well as concentrations.

A computer 30 receives and processes the signals into a series of peaks (called "components") representative of the sample constituents, the plotted locations of the components representing corresponding retention times. The computer presents (e.g. on a monitor) corresponding retention indicators which may be the retention times directly or other indicators computed from the times such as retention indices (explained below). The peak components may be identified by an operator or the computer to known chemical constituents, and peak heights provide a quantitative measure.

The computer system 30 is conventional and actually may be a combination of processing units including a main computer such as a DEC PC LP433 incorporated into the GC by the manufacturer thereof. Auxiliary processing units may include one for automatic sample selection, another for controlling the oven, and another for communications and pneumatic controls. These units communicate to the main computer via an interface processor. Each unit may include appropriate firmware. As this computer system is conventional, and the details are not important to the present invention, except for an oven controller 46 it is depicted as a single computer 30 in FIG. 1. Thus the computer generally includes a central processing unit 32 (CPU) with associated memory 34 (RAM); appropriate analog/digital converters (in and/or out as required); disk memory sections (more generally a computer readable storage medium) typically including a hard disk 36, laser disk (CD-Rom) and/or means for accessing a floppy disk 38, a keyboard 40 for operator input, and a monitor 42 and/or a printer for presentation of the retention indicators.

The computer programs for the standard GC operations and the present invention are written in a conventional language such as "C", "C++", Visual Basic™ and data is managed by a spreadsheet program such as Excel™. Programming required for the present invention will be recognized readily from the flow charts and descriptions herein, and can be achieved by those of ordinary skill in the art.

The column 18 is enclosed in an oven 44 or the like with the controller 46 to set and regulate the temperature of the column. The temperature is measured with a platinum resistance thermometer 48 (or other precision temperature sensor) with a temperature signal being passed on a line 51 to the computer 30. Retention times are temperature dependent, so data usually are taken at one or a series of known temperatures, optionally with ramping or other temperature program during a run. Similarly, the retention times are pressure dependent, and the data also may be taken at one or a series of known pressures, optionally with ramping or other pressure program. With ramping, the associated parameters include start and finish values as well as ramping rate and start or finish time for the ramping.

The term "program", as applied to temperature, pressure or other such parameter, and as used herein and in the claims, means a fixed level (e.g. isothermal or isobaric) or a varying of such parameter with time during a run with an injected sample. "Ramping" is typically but not necessarily a linear change, usually increasing, and a program may combine fixed levels and ramping, and may include several rampings.

Thus operating parameters for the system typically include isothermal or other programmed temperature of the chromatographic column, constant or other programmed inlet pressure to the column, and composition of carrier gas (which may be a fixed or variable mixture, for example, of methane/argon or $N_2$/Ar). Other program parameters may include ramp rates, starting and final temperatures and/ or pressures, times at each level, and/or initial and final times for the ramping. A program may be more complex, such as with several fixed levels with ramping between, or nonlinear changes.

Pressure at the column outlet generally is atmospheric, or may be vacuum where the GC is used, for example, in conjunction with a mass spectrometer. The outlet pressure $P_o$ is measured with a barometer 49 but ordinarily is not regulated. However outlet pressure could be reset or varied as part of a pressure program. Another possible operating parameter may be column length taken from its categorization as a column dimension (described below), as the column length is readily measured and the column may be cut successively for a series of system runs, particularly with the primary system discussed below.

Use is made of theoretical relationships that describe operation of a GC, in the form of a mathematical function. A suitable function is expressed by or derived from an integral:

$$\int_0^{t_R} t_0^{-1} \cdot (1 + a/\beta e^{b/T+cT})^{-1} \cdot dt = 1 \qquad \text{Eq. 1}$$

where:

$$t_0 = 32 \cap(T)/3 \; L^2/r_c^2 \; (p_i^3 - p_o^3)/(p_i^2 - p_o^2)^2 \qquad \text{Eq. 1a}$$

and $t_R$ is retention time, T is column temperature, $\cap(T)$ is carrier gas viscosity as a known function of temperature, L is column length (FIG. 2), $r_c$ is column radius, $p_i$ is inlet pressure and $p_o$ is outlet pressure. The term $t_0$, variously called dead time, mobile phase time or gas holdup time, represents the time of the pulse in the carrier gas. The term $\beta$, called phase ratio, is the ratio of volume of the mobile phase (carrier gas) to that of the stationary phase, such that $\beta = r_c/2d_f$ where $d_f$ is thickness of the stationary phase on the column tube wall. Column dimensions for the column geometry are in the function as L, $r_c$ and $\beta$. The thermodynamic constants a and b are related to enthalpy and entropy and, without the constant c, were discovered to be slightly temperature dependent. To substantially remove this dependency, the additional thermodynamic constant c is introduced, and all of a, b and c are deemed to be constant for each sample component, (but generally are different for different components and stationary phases. However, c may be quite small and even assumed to be zero if resulting accuracies are sufficient. Eq. 1 is used conventionally without the c term which is added according to an aspect of the present invention. Temperature and/or pressure may vary with time during a run, so solution or application of the integral depends on which and how these parameters are so varied during the integrating time from 0 to $t_R$.

For constant temperature and pressures the function may be integrated to a form:

$$t_R = t_0 \cdot [1 + a/\beta e^{b/T+cT}] \qquad \text{Eq. 2}$$

This may used for constant (isobaric and isothermal) conditions or fixed portions of programs. Otherwise Eq. 1 is solved by a conventional computational technique such as with Simpson's rule using, for example, 20 steps.

Any other suitable function that describes chromatography may be used in place of these equations. Such function preferably is based on the physics of chromatography but may include or be based on empirical factors. For example a modification of the function may be made to compensate for slight leakage of the carrier gas through the column wall, such as taught in copending provisional U.S. patent application Ser. No. filed Apr. 15, 1997 [Docket No. ID4531] entitled "Method and Apparatus to Compensate for Chromatograph Column Permeativity", by inventors Jerry E. Cahill and David H. Tracy of the present assignee and incorporated herein in its entirety by reference.

The function (e.g. Eq. 1 or 2) is stored in computer memory in the form of program code (for the function itself) and data code (for the parameter data). With either form of the function, the independent variable of the function preferably (and in the present example) is the column temperature T (or program thereof), with function parameters including the inlet and outlet pressures $P_i$ and $P_o$, the column geometry $\beta$, L and $r_c$, and the thermodynamic constants a,b,c. Alternatively, the inlet pressure may be useful as the independent variable in place of temperature which becomes a function parameter. More broadly, any of the operating parameters may be used for the independent variable, and there may be more than one independent variable such as temperature and its ramp rate, or temperature and pressure.

To implement the invention, with reference to the flow chart FIG. 3, a primary chromatographic system 52 is provided which should be of the same general type as a target system (discussed below) including substantially the same type of column. The primary system has established (assumed or known) primary column dimensions for its chromatographic column. Such dimensions include the average thickness $d_f$ of the stationary phase on the column wall (FIG. 2), the column length L, and the column radius $r_c$, thereby establishing the phase ratio $\beta = r_c/2d_f$. The thickness may be measured, for example, by weighing of the tube during manufacture (before and after packing). Alternatively, the column dimensions may be determined after initial measurements with the primary system, by destruction of the column for measurement of the thickness and radius, as this column will no longer be needed. For a packed column, the volume of the stationary phase may be used as a geometry dimension.

A standard sample 54 is selected to contain suitable constituents to span the range of expected interactions of actual samples with the stationary phase. A standard with about 8 to 10 compounds is useful. The compounds should be selected for suitability with the stationary phase, for example in a manner taught in an article "Characterization of Some Liquid Phases" by W. O. McReynolds, J. of Chromatographic Science 8, 685–693 (December 1970), incorporated herein by reference. A suitable standard for a stationary phase of methyl silicone contains the following: n-nonane, 2-octanone, n-decane, 1-octanol, n-undecane, 2,6-dimethyphenol, 2,4-dimethylanaline, naphthalene, n-dodecane, and 2-propanol as solvent.

The primary system 52 is operated 53 with the standard sample 54, a primary inlet pressure 56 (or, more broadly, a primary pressure program), and with a successive plurality of selected temperatures 58 for the temperature. Each temperature program may simply be an isothermal temperature level, or may consist of programming parameters for a run such as initial and final temperatures, ramping rate and initial and final times for the ramping; any one or more of these parameters may be varied for successive runs. Selection of temperature programs should depend on such factors as intended types of application samples and intended temperature ranges and programming. Examples of four programs are as follows; the first also shows how the selected programs can be useful for auxiliary purposes explained below:

1) 120° C. for temperature calibration, phase ratio, selectivity validation; 250° C. for temperature calibration; Ramp 80° C. to 250° C. at 5° C./min, for effective column length.

2) Isothermals at 80° C. to 100° C. in 10° C. steps.
3) Isothermals at 250° C. to 300° C. in 10° C. steps.
4) Ramp from 80°C. to 250° C. at 5° C./min; ramp from 80° C. to 250° C. at 10° C./min; ramp from 80° C. to 250° C. at 15° C./min.

This operation generates a set of primary retention times (RT's) 60 (which may be converted to other related retention indicators) for each temperature program, which may be plotted as a primary chromatogram (e.g. FIG. 4) with a component 61 (peak) for each constituent in the standard sample. These components are identified 62 by operator or a computer program in the conventional manner by comparison with a list of expected times in a pre-established order, accounting for temperature and rejecting noise peaks. It is advantageous to pick one standard time and ratio the other times to that for the selection process.

For each component from the standard, the primary retention times and the primary temperatures (or programs) are fitted 64 to the function 66 (Eq. 1 or 2). The computations for the fitting determine the thermodynamic constants a,b,c (68), such that the function relates retention time to column temperature, pressure and column geometry. All other function parameters are known, including the primary column dimensions 70. The thermodynamic constants are different for each component, i.e. each constituent of the sample, and are specific to the chemistry of the stationary phase. The number of temperature programs needed for a fit is at least as many as there are number of thermodynamic constants. (A fitting technique—"Application of Function"—is set forth below.)

The function with the computed set of thermodynamic constants may be identified to a virtual (hypothetical) chromatographic system 69, with the pressure and column dimensions being adjustable according to variations in target systems. The primary system and its column are no longer needed. This virtual system is deemed to be a standard to compare with other GC systems (herein designated "target chromatographic systems") that are similar to the primary system, particularly with the same type of column including stationary phase.

Figure 4:
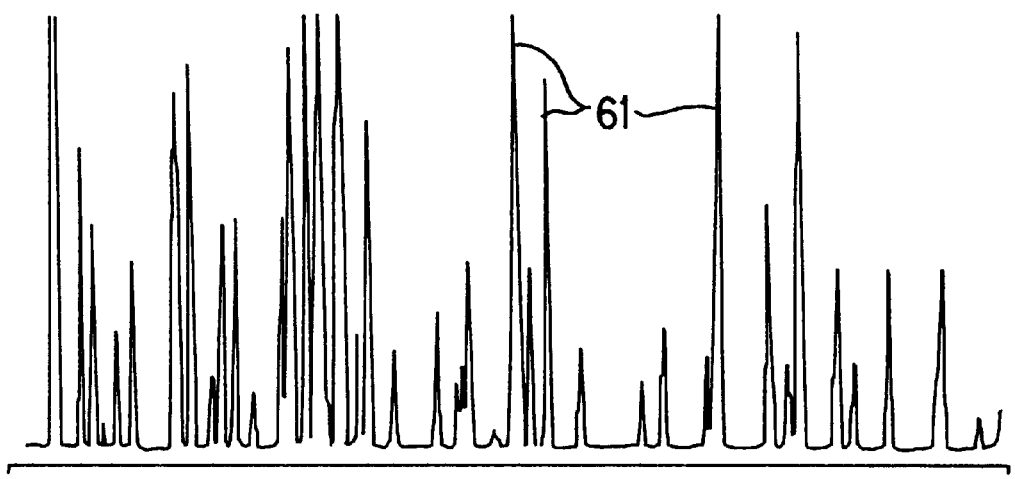
FIG. 4 is an illustration of a series of peaks representing chromatographic retention times of constituents such as from a sample utilized with the system of FIG. 1.

A combined plot from the functions for all components yields a simulated chromatogram of the virtual system which essentially will look like FIG. 4. (Peak heights may be selected arbitrarily to be different for the components to aid in identification. Peak width is programmed to be similar to that of actual peaks.) A floppy disk 71 (or other computer readable storage medium such as a CD-ROM or tape) containing the thermodynamic constants may be provided along with an associated column and a standard sample. The storage medium may also contain the program base for the function if this is not already in the instrument computer.

A target chromatographic system 72 is operated 73 with the standard sample 54 (meaning the original or a substantial duplicate thereof), and with a pressure program setting 56' substantially as the same primary inlet pressure 56 (or other pressure program); this pressure may not be quite the same as the primary due to variations in system and settings. However a pressure calibration step is desirable for example by fully opening the flow valve 19 (FIG. 1) at the split flow exit and stopping carrier flow with the flow control 14 so as to expose the pressure gage to atmospheric pressure and use this as a zero calibration point 75 (gage pressure).

A set of temperature values 74 is selected, which do not need to be the same as the primary temperatures. Suitable temperature programs are two fixed (isothermal) levels at 120° C. and 250° C., and a ramping from 80° C. to 250° C. at 5° C./minute. Corresponding secondary retention times 76 (or other retention indicators) are determined for the selected temperature programs. The isothermal retention times have several uses including standardization of systems, temperature calibration, validation and determination of phase ratio.

The temperature scale of the target system should be calibrated 78 to effect calibrated temperatures 79, for example in a manner described below using a secondary retention time for an isothermal for a specified component. Also, at this stage, a validation 80 of the target system (primarily to validate the stationary phase composition) is desirable, also as described below. If validation does not pass, further procedures are terminated to locate and fix 82 the problem, e.g. change columns.

It is necessary to determine the parameters associated with column dimensions of the target system. There may be circumstances where the column dimensions for the target system are already established, e.g. in a prior run or by measurements during manufacture such as measuring the exact amount of stationary phase retained in the column. In this case the following procedure to determine column dimensions with the function may be skipped.

The secondary retention times 76 are identified as target times for the function (Eq. 1 and/or 2). The target system (particularly the target column) is characterized 84 by reverse application of the function 66, to determine effective column dimensions 86 for which a computation with the function yields substantially each secondary retention time for the temperature at which the target system was run, using the previously determined thermodynamic constants 68 and the primary inlet pressure 56. The phase ratio may be determined with the function; however, as explained below, the phase ratio β advantageously is determined from retention times, so only a parameter associated with length L (viz. L itself or aspect ratio $L/r_c$) needs to be determined with the function.

Next, an effective secondary program for inlet pressure 88 is determined 90, again by reverse application of Eq. 1 and/or 2, for which, with the effective column dimensions 86 and the previously determined thermodynamic constants 68, the function yields substantially the primary retention times 60 for any temperature program, preferably one of the nominal selected temperature programs. A fixed pressure may be suitable, or a pressure program such as ramping may be advantageous to achieve suitable equality of retention times. This secondary pressure program 88 may be used 87 in subsequent system operations, or a selected program may be used by calibration.

For such a selected pressure program, a fixed pressure for the program 88 also provides a second calibration point for effective inlet pressure of the target system, compared to the pressure setting for the target system. With this point and the first calibration "zero" point 75 determined as described above, and with assumed linearity, a pressure calibration 87 is established. Any operating pressure 89 ($P_i$, fixed or otherwise) may be selected for subsequent operations of the target system. The proper pressure program setting corresponding to the operating pressure program is ascertained from the calibration. Using the same procedures with other chromatographic systems operated for the same selected, calibrated pressure, retention times may be compared directly The actual pressure settings for the other systems would be determined, calibrated and scaled in the same manner as in the present case.

In the foregoing, an ideal goal is to determine the effective column dimensions and the secondary inlet pressure such that the function yields retention times exactly equal respectively to the secondary and primary retention times. As this generally is not quite attainable, the clarification "substantially" is intended to mean within practical limits of attainability. Details for application of the function are provided below.

The target chromatographic system 72 then is operated 91 for sample analysis, using an application sample 92 (usually unknown). For operating parameters, the selected pressure program 89, and any selected program (fixed or ramping) for the temperature 94 are used, preferably with temperature calibration 78. Such operation generates at least one test retention time 96 for each component and each temperature program. By use of the secondary pressure program (fixed or ramping), the test retention times are thereby standardized to the virtual chromatographic system 69, and may be utilized for analysis 98 of the application sample. Similar operations with other application samples and other target systems provide retention times that, after normalization to a selected temperature by use of the function, may be compared directly. This also allows computer comparison and identification with a library of such times for selected chemical constituents.

In the foregoing, temperature is selected conveniently as the independent variable with the pressure program as a parameter in the function. These roles could be reversed, with pressure as the independent variable. More broadly, any of the other operating parameters could be used in these roles, namely outlet pressure, ramping rates and times (or other program parameters), carrier gas composition (affecting viscosity $\cap$), column length, and even another column parameter such as stationary phase composition or thickness if such can be varied controllably for a set of runs. Moreover, more than one of these variables could be used in each role at the same time, e.g. adding ramping to temperature. As used herein and in the claims the term "first parameter" means the independent variable (temperature in the above example), and "second parameter" means the parameter (e.g. inlet pressure) that is adjusted to standardize the target system to the virtual system.

As the function (Eq. 1 or 2) of the present embodiment includes inlet pressure, it is preferable that the system utilize back pressure regulation of the split flow so that inlet pressure be controlled and known directly. However, the invention could be utilized with flow regulation of the split flow such as disclosed in Hinshaw 1, provided inlet pressure to the column is measured and preferably is reproducible. Alternatively, with such a flow regulation system, a function may be derived with column flow rate as a first or second parameter in place of pressure, such flow rate being reproducible and measured directly or ascertained by subtraction.

The invention may be used with a supercritical fluid for the carrier. In this case the term "gas" herein includes such fluid and the procedures are substantially the same as described herein including use of the same or other suitable function that describes the chromatography. The invention also may be utilized in a liquid chromatographic (LC) system with a liquid carrier such as the type described in the aforementioned U.S. Pat. No. 4,579,663. For LC additional consideration is given to interactions of the sample with the liquid carrier.

Column Dimensions

Characterizing 84 the effective column dimensions 86 (FIG. 3) for the target column conveniently has two aspects. The phase ratio $\beta$ may be determined directly from a retention time. Other column dimensions are ascertained as described below by application of the function.

Phase ratio $\beta = r/2d$ in the primary dimensions 70 for the primary column ($\beta_p$) preferably is determined from actual measurements on the column, by destruction if necessary. Although the measurements should be as accurate as practical, absolute accuracy is not necessary because, in the characterization 84 for target column dimensions 86, the phase ratio for target columns ($\beta_t$) is determined relative to a known $\beta_p$. The phase ratio also has a relationship $\beta = K/k$ where k is a capacity factor and K is a partition coefficient that is constant for a given component, stationary phase and temperature, so that $\beta$ is inversely proportional to k. The latter is calculated from $k = (t_R - t_o)/t_o$ where $t_R$ and $t_o$ respectively are retention time and mobile phase time as defined above. The capacity factor k can be calculated from any of the isothermal retention times taken with the primary and secondary system in the course of the other procedures. The phase ratio for the target column is related to that of the primary column by $\beta_t = \beta_p \cdot (k_p/k_t)$. This is used to compute the phase ratio for the column of each target system and is entered into the function prior to determination of the aspect ratio. The latter is determined from the function as explained below.

Application of Function

The integral function (Eq. 1) is sufficiently complex for there to be no apparent analytical solution, so that special techniques generally are required for its application. Any standard or other desired mathematical techniques may be used. In one preferred approach, the dead time $t_0$ is first determined by using a set of certain homologous standards such as n-alkanes, the set advantageously being included in the standard sample 54 (FIG. 3). Each homologous standard has a unique homolog number, such number being an integer number $C_n$ of carbon atoms for the n-alkanes. About five or six such alkanes with contiguous numbers are suitable, such as those having known $C_n$ numbers from 6 to 10. Retention time $t_R$ is related to this number by a homolog relationship:

$$\ln (t_R - t_o) = g \cdot C_n + h \qquad \text{Eq. 3}$$

where $t_o$ is time in the mobile phase ("dead time"), and g and h are homolog parameters that are potentially temperature dependent. Other homologous standards may be used, provided they have identifiable equivalent numbers (not necessarily integers) in a similar relationship. Determination of standard retention times $t_R$ for the alkanes is included in the operations of the primary system, for at least one selected temperature. The dead time and constants are determined by fitting the equation to the measurements of $t_R$.

Figure 5:
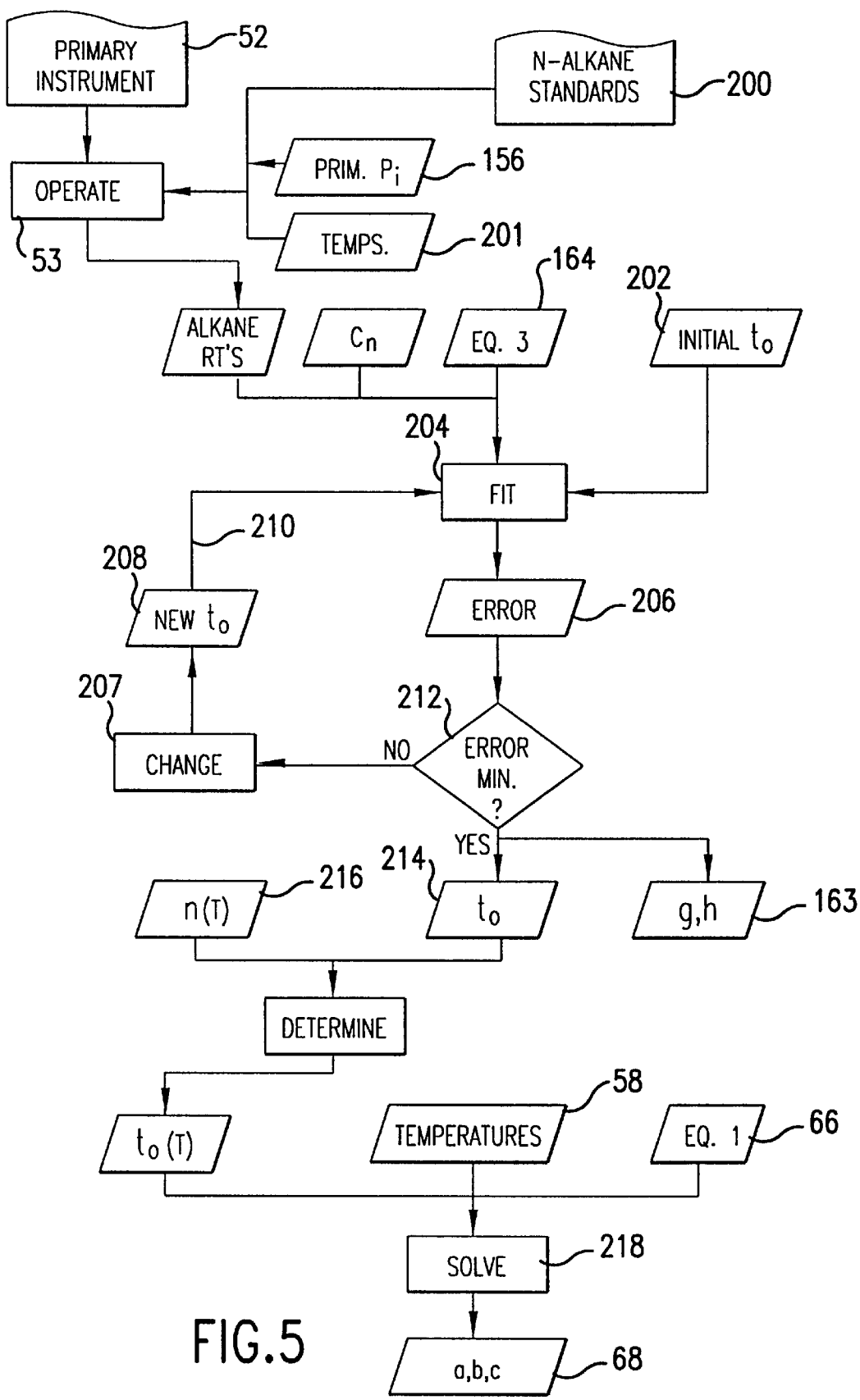
FIG. 5 is a flow chart of a method and a means for applying a function in the embodiment of FIG. 3.

To do this (FIG. 5), the primary system 52 is operated 53 as before with a sample 200 containing the n-alkane standards (or other homologous standards) using the primary pressure 156 and one of the selected temperatures 201 to generate alkane retention times 158. Utilizing Eq. 3 (164) an algorithm inserts a selected initial value 202 for $t_0$ and performs a linear least squares (or other statistical) computation to fit 204 the data to generate the constants and a statistical error factor 206 for the fit. The dead time is changed incrementally 207 to a new $t_0$ 208 and the process is iterated 210 until a first value of $t_0$ 214 for each selected temperature is found 212 that minimizes the error within a preset limit and thereby gives a "best" statistical fit. This also determines the parameters g and h (163).

As pressures are the same for the several isothermal operations, it may be seen from Eq. 1a that $t_0$ is proportional to carrier gas viscosity $\cap(T)$ which is temperature dependent. A data base is stored 216 in the computer for the viscosity over the desired temperature range, conveniently in the form of parameters for a function relating viscosity to temperature. Values for other dead times $t_0$ are obtained for the other relevant temperatures in proportion to the viscosities at the original and the other temperatures to effect the temperature dependent $t_0(T)$. With these dead times, Eq. 1 is integrated (e.g. with Simpson's method) over the three temperature programs for the standard compounds, to provide three equations to solve 218 for the three thermodynamic constants a,b,c.

For the dimensions 86 (FIG. 3) of the target column, the phase ratio β is determined as explained above. The column length appears in Eqs. 1 and 2 via Eq. 1a as an aspect ratio $\alpha = L/r_c$. Thus either this ratio may be determined as a length parameter, or $r_c$ may be estimated and an effective value for L determined (which corrects for any inaccuracy in $r_c$). Conveniently the length L is taken to be the parameter.

A searching technique may be used for solving the function to determine one or more parameters such as the length L. A suitable technique (FIG. 6) for solving the function involves utilizing a stored initial parameter data base 102 defining tentative values of the length (or other parameter) within a predetermined range over expected operating conditions, such as from 20 m to 40 m in 1 m increments for a column having a nominal length of 30 m. (The data actually stored may be the lowest and highest lengths plus increment value.) Other parameters 104 are known, namely the thermodynamic constants 68 (FIG. 3), set pressure 56, calibrated temperature 79 and phase ratio β. With the function 66 (e.g Eq. 1), theoretical retention times 106 are computed 108. Differences 110 ("errors" or "residuals") between the theoretical times and measured times 76 are calculated 112. This is done for each value in the length base and for each of the sample components, and is presented advantageously in the form of root-mean-square ("rms") residuals.

The residuals may be plotted against the parameter if desired, or as contours if there are several parameters in the search, using conventional techniques. Such plot may be useful in visualizing a search, but is not important to the present invention.

A search for the minimum may be done manually (e.g. by pointing and clicking an appropriate monitor display of a plot of the residuals vs. length) or with any available or other desired computer program. An initial coarse search 122 is advantageous, if not done previously 124, to find the region containing the lowest minimum. There may be mathematically forbidden areas in the range ("fractal space") which, if found, are assigned an arbitrarily high value such as 1000. The minimum residual 120 then is determined. (Although not likely for the length L, in other applications for the searching there may be several minima, and the coarse search should find the lowest.) A revised (narrowed) length data base 126 with a smaller range such as 2 m around the minimum residual is selected 129, Eq. 1 is applied again to compute 108 theoretical retention times 106, and residuals 110 from the measured values 76 are recalculated 112.

When a coarse search cycle 123 is determined 124 to have been done a set number of times (once should be sufficient), a fine search 128 is effected in the revised matrix 126 for the selected region so as to zero in on the minimum in the selected well. This may be done conventionally such as with linear programming, simulated annealing or, advantageously, an adaptive non-parametric search such as an algorithm for a downhill simplex method described in "Numerical Recipes in C" by W. H. Press, S. A. Teukolsky, W. T. Vetterling and B. P. Flannery, The Art of Scientific Computing, 2nd ed., Cambridge University Press (1992). A conventional simplex search program determines the average of the residuals for two proximate points that define a short line. The program flips the line over one of the points, redetermines the average and whether it has reduced; if not the line is flipped over to the other way. The procedure is repeated in search of lower residuals 129. An advantageous modification to the simplex search shortens the point separations by a preset factor when the residual average is reduced, or lengthens the separations by such a factor when a residual average increases, for example by a factor of two in each case. The starting points may the previously determined minimum and the next best point.

When a low residual 129 is found reflecting a "well", a test 130 for a nearly flat bottom of the well is made for the rms residual not to change more than a preset limit such as 0.00001. If this is not met, the simplex cycle is repeated 133 with a revised data base 126 of lengths selected 129 in smaller intervals around the latest region. If the number of simplex cycles exceeds a limit 134 such as 500 cycles, a problem is assumed to exist and the program is terminated 136. Otherwise the last low residual is selected as the minimum 131 and this determines 137 the corresponding column length L or other parameter.

Figure 3A:
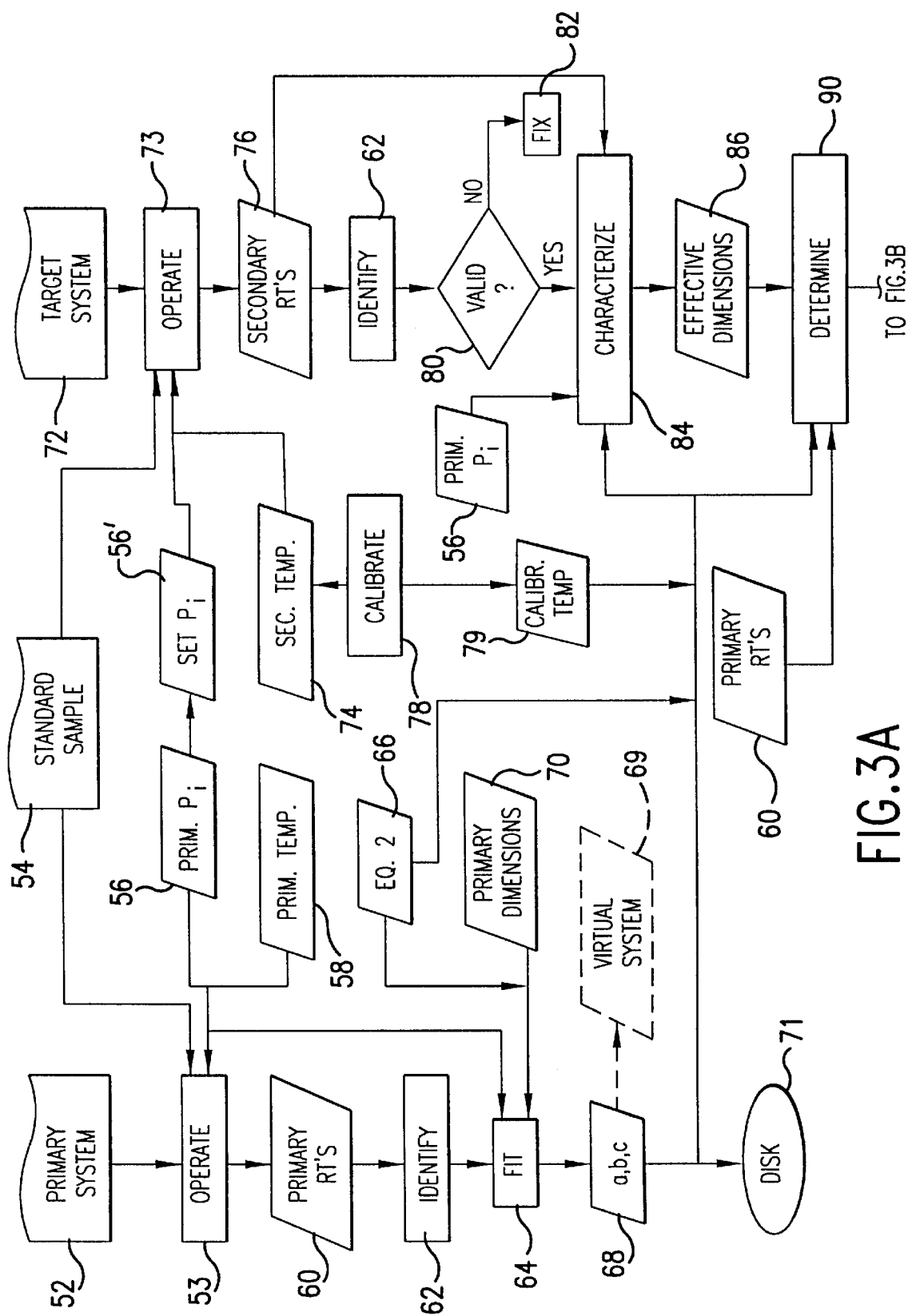
FIG. 3A and FIG. 3B are a flow chart of a method and a means for carrying out an embodiment of the invention for standardization of a system of FIG. 1.
Figure 3B:
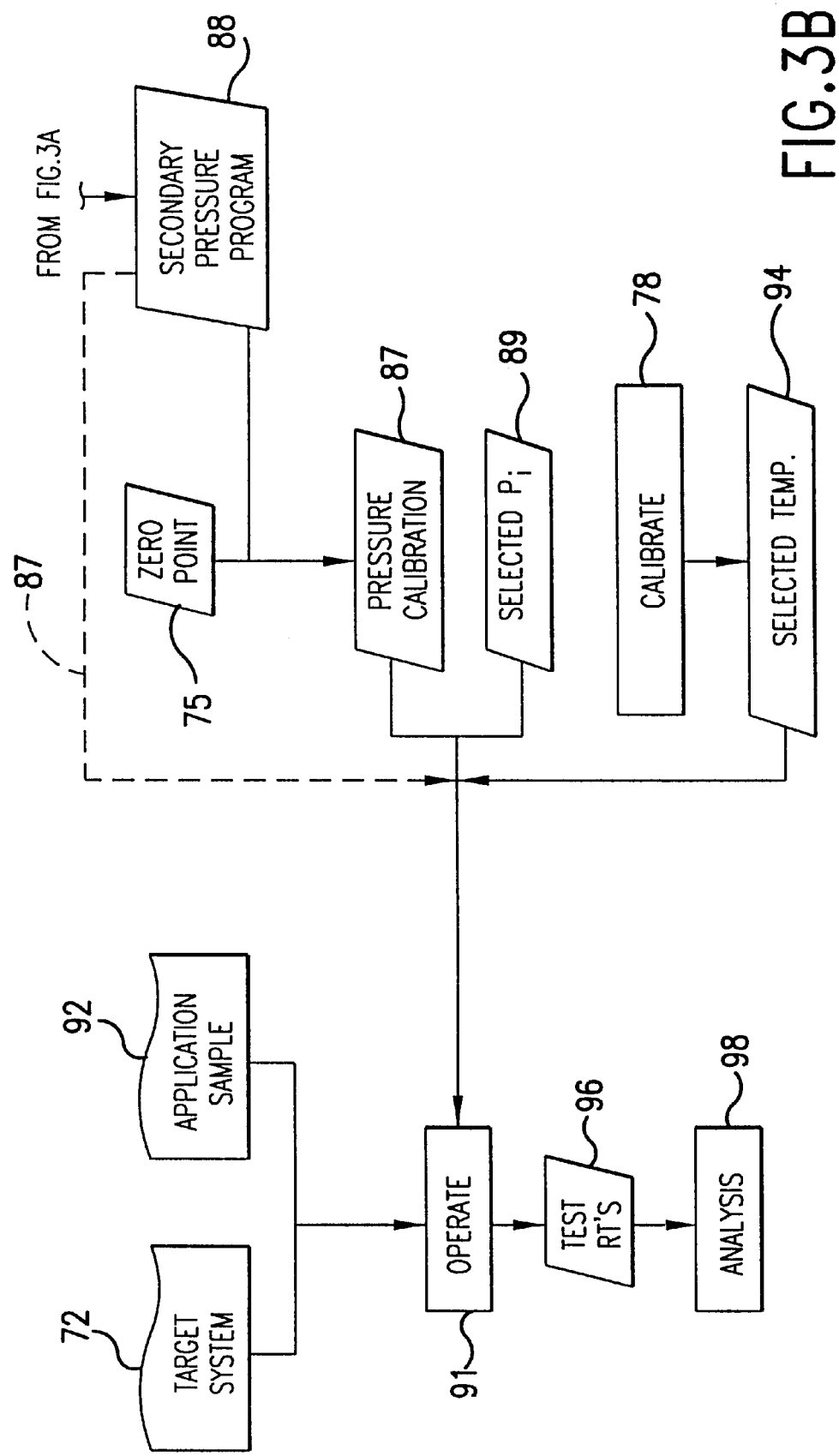
Figure 6:
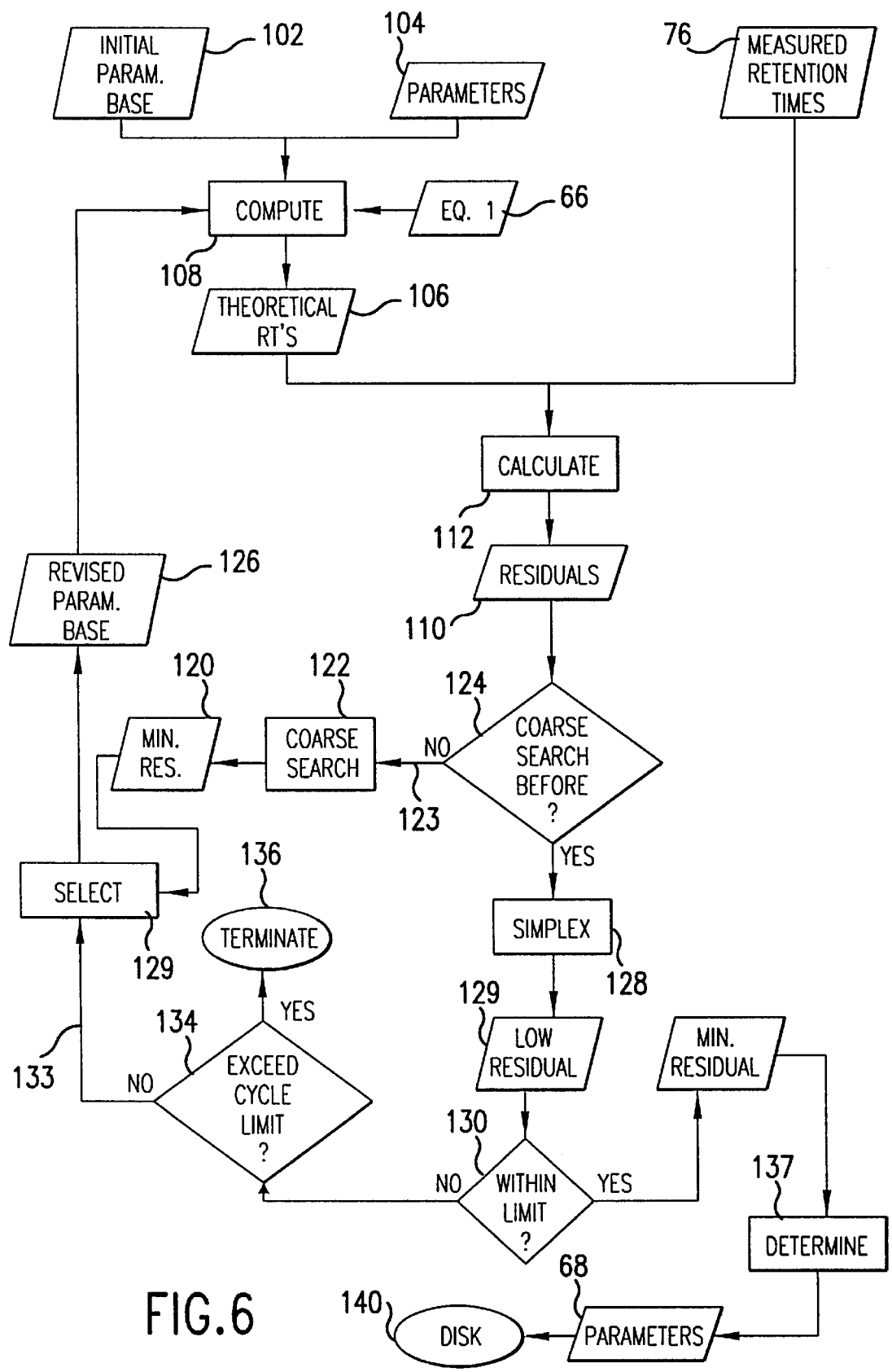
FIG. 6 is a flow chart of an additional method and an additional means for applying the function in the embodiment of FIG. 3.

A similar procedure may be used to apply the function with coarse and fine searching to determine 90 a secondary pressure program 88 (FIG. 3). If this is a fixed pressure, an initial data base of a range of potential pressures is used for the initial parameter base 102 (FIG. 6) in place of the initial length base, the length L and radius $r_c$ replace the initial pressure as predetermined parameters, and the measured retention times are the primary retention times. Otherwise the procedures of FIG. 6 are substantially the same. In the case of pressure or some other parameters, there may be several minima from which the coarse search serves to select a lowest minimum before the simplex search.

In the case of a pressure program with ramping, the procedures are effected with a matrix of parameters associated with the program such as ramp rate and initial and final pressures (thus a 3-dimensional matrix). More broadly, the matrix has as many axes as variables being considered, e.g. one, two, three or more. Residuals are computed for all of the compatible combinations in the matrix. For the coarse search, the residuals are searched by computer program to find the low in the same manner as described above. For a simplex search with a two-axis matrix, three proximate points are used in place of two for the averaging of residuals, and a triangle is visualized in place of the short connecting line. In the search the triangle is flipped over one of its sides for recomputation of an average. For a three-axis matrix, a pyramid is visualized with similar flips over an edge.

The plotting and searching technique may be used for broader purposes, for example for an operator of a chromatographic system to optimize selected operating parameters without necessarily being for the forgoing standardization to a virtual system. In the broader case, the system has operating parameters including selected parameters for optimization and remaining parameters, and operation of the chromatographic system is represented by a mathematical function having function parameters including the operating parameters. The primary chromatographic system is operated with a sample and selected values for the operating parameters so as to generate corresponding measured retention indicators. A data set or matrix is provided comprising potential values of the selected operating parameters over predetermined ranges of such parameters in predetermined increments, the data set representing combinations of such parameters. Theoretical retention indicators are computed with the function for the combinations of such parameters and for the remaining parameters which are known or assumed for the purpose of the computation. Differences (residuals) between the measured retention indicators and the theoretical retention indicators are computed. The residuals are searched for a minimum in the differences, such that the minimum establishes optimized selected parameters. The system then is operated with the optimized parameters.

It may be desirable for a plot of the retention times (actual and simulated) at each stage to be displayed on the monitor for operator viewing. Operator instructions for proceeding may be entered by way of pop up menus. Software (or firmware) with the function and the residual plotting and searching means for applying the function, along with matrix data, may be incorporated into the computer programming of the system, or may be provided separately such as on a floppy disk.

It is intended, as an aspect of this invention, that the foregoing searching technique may also be used directly for determining one or more optimum operating parameters for a chromatographic system, independently of any standardizing.

Column Temperature

Temperatures for the primary chromatographic system should be measured as accurately as practical by conventional means, such as with several thermocouples distributed in the oven near the column and allowing the system to stabilize at each temperature. Ultimately, however, the primary system temperatures may be considered to be standard, and absolute accuracy is not critical, as long as temperatures of subsequent system columns are accurate relative to the original temperature scale of the primary.

The operating temperatures of the target column should be determined with precision relative to the temperature scale of the primary system. Calibration of temperature for the target column, according to an aspect of the invention, is made with use of a selected calibration compound. For this, it is advantageous to express the retention indicator in an alternate form "retention index" RI, also known as "Kovats Index", as for example in the following references: E. Kovats, Helv. Chim. Acta 41, 1915–1932 (1958); E. Kovats, Z. anal. Chem. 181, 351–366 (1961); P. Toth, E. Kugler, and E. Kovats, Helv. Chim. Acta 42, 2519–2530 (1959); A. Wehrli and E. Kovats, Helv. Chim. Acta 42, 2709–2736 (1959); L. S. Ettre, Anal. Chem. 36 (8), 31A–47A (1964); E. Kovats, in Advances in Chromatography Vol. 1 (J. C. Giddings and R. A. Keller, eds.), M. Dekker, Inc., New York, 1965; pp. 229–247. Retention index is defined as $RI=100 \cdot C_n$, where $C_n$ is a number associated with n-alkanes (or other standards) described above with respect to the homolog relationship Eq. 3 which thereby becomes:

$$RI=(100/g)\cdot[\ln(t_R-t_o)-h] \qquad \text{Eq. 4}$$

Any arbitrary compound (other than an n-alkane) has a retention index corresponding to a generally non-integer $C_n$ determined from Eq. 4 by measurement of retention time. The retention index for such a compound thus is relative to the alkane standards, and is substantially independent of most parameters except temperature. This allows the retention index to be used in systems with varying parametric conditions while determining temperature dependence. To the extent that the retention index has a minor dependence on such parameters as pressure, such parameters should be repeated as closely as practical for successive runs.

For an aspect of the present invention, at least one temperature calibration compound is selected, the compound preferably having a retention index that has a relatively strong dependence on temperature. This compound is included in a temperature standard sample with the several homologous standards (e.g. alkanes). To cover a desired temperature range it may be desirable to utilize two or more such compounds such as naphthalene and anthracene, each being most effective in a separate, narrower range for the temperature calibration, e.g. 120∘ C. and 250∘ C. respectively.

Advantageously the temperature standard sample (with alkanes and calibration compounds) is included with in the standard sample with the constituents used to define the virtual system, so only one set of runs is necessary, and temperature is calibrated simultaneously with test operations. All or some of the calibration compounds and alkanes may even be used for such constituents, except to define the virtual system it may be advantageous to use other constituents that have less temperature dependence. Moreover, such other constituents may better simulate the range of application sample materials likely to be tested.

To establish temperatures, (FIG. 7), the primary chromatographic system 52 is operated 53 with the temperature standard 152 at a plurality of selected calibration temperatures 154 for the column and with a selected pressure program 56. (For convenience these are included in the same conditions as for the standardizing runs, with the temperatures used here being one of the isothermal runs. The number of temperatures depends on the number of constants in Eq. 5 below, being three in the present case.) This generates a primary set of retention times for each temperature, comprising homolog (e.g. n-alkane) retention times 158 for each of the calibration compounds and a compound retention time 160 for the temperature calibration compound. After peak identification (not shown) the homolog retention times and the known retention indices $C_n$ for the standards are used to determine 162 homolog parameters g and h (163) for the established relationship 164 (Eq. 3), relating homolog numbers to retention indicators (e.g. indices), these parameters being temperature dependent. A primary retention index 166 for the calibration compound is calculated 168 from the relationship 164 (Eq. 4) with the parameters g, h and the compound retention time 160 for the each calibration temperature, thereby relating a homolog number at each temperature for the calibration compound to its retention index. The term $t_0$ in Eq. 4 is determined as described above. This homolog number is associated with the calibration temperature $T_c$ (154). A temperature relationship 170 between retention index and temperature is close to being linear with temperature, but a quadratic fit may be used for accuracy:

$$RI=u+vT_c+wT_c^2 \qquad \text{Eq. 5}$$

where u, v and w are calibration constants 174 that are calculated 172 from the retention indices and temperature data. Several (three in the present case) primary temperature runs with different calibration temperatures are needed to get these constants; again these may be combined with the original runs. These constants may be included in a data disk (or other such medium) along with the program base for Eq. 5 if necessary. Advantageously this is the disk that also contains the data base for the virtual system.

The target chromatographic system then is operated 73 with the primary pressure program 56 and a selected secondary temperature 180 (or two such temperatures if two calibration standards are used), and with the sample 152, so as to generate a corresponding test set of retention times. The temperature 180 is measured with the scale (which may be arbitrary) associated with the target system. This operation is a temperature calibration run that for convenience could be the same as one of the runs for the standardization. These times comprise alkane retention times 182 and a compound retention time 184. The alkane retention times are used to redetermine 162 new homolog parameters g and h (188) for the established relationship (Eq. 3), and calculate 190 a secondary compound retention index 192 from the relationship 193 (Eq. 4) and the new parameters. The calibration relationship Eq. 5 (170, FIG. 7), with its earlier-determined constants 174, is applied with the calculated retention index 192 to determine 194 the calibrated column temperature 79 for continuing with other procedures (FIG. 3), related to the primary system, that existed at the time of operation the target chromatographic system. If desired, a series of these temperatures may be determined to calibrate the temperature sensing system on the target system, so that the sensor may be used directly thereafter.

Although retention index is a preferred form of retention indicator for the temperature calibration, as it simplifies the computations, other forms could be used. The retention indicator is advantageously in a form that is substantially independent of system parameters and operating parameters other than temperature, the homologous standards each having a predetermined retention indicator in such form. Also, the temperature calibration may be achieved with one or more other homologous standards in place of the n-alkanes described above, provided such standards have a known, established relationship to their retention indicators.

It is intended, as an aspect of this invention, that the foregoing technique for temperature calibration may also be used directly for calibrating a chromatographic system, independently of any standardizing.

Validation

Figure 8:
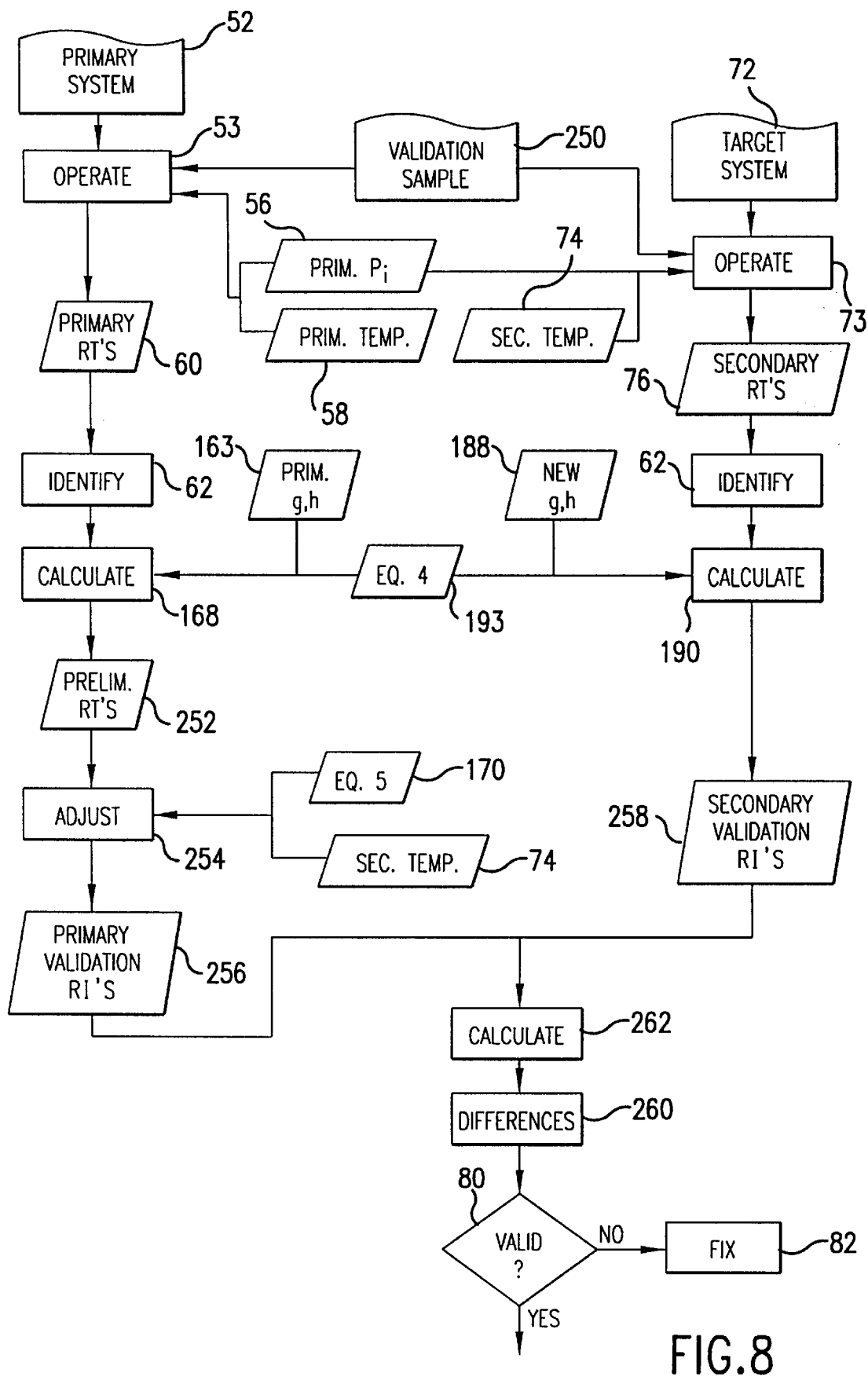
FIG. 8 is a flow chart of a method and a means for validating the system of FIG. 1.

It is desirable to validate the target system, to ensure particularly that the target column is of the type intended and in satisfactory condition, and more particularly that the stationary phase chemistry ("selectivity") is satisfactory. Such validation (80 in FIG. 3) may be effected with reference to FIG. 8. A validation sample 250 has a set of selected validation constituents which may be included in the standard sample, and advantageously are the same as the constituents used for standardizing.

Thus, as before, and conveniently during respective operations 53, 73 of standardizing runs with the primary and target system 52, 72, the primary validation retention times 60 and the secondary validation retention times 76 are obtained and identified 62 for the validation sample constituents 250. The temperature programs 58, 74 each preferably includes an isothermal run (advantageously one of the original runs) with a primary validation temperature for the present case.

Figure 7:
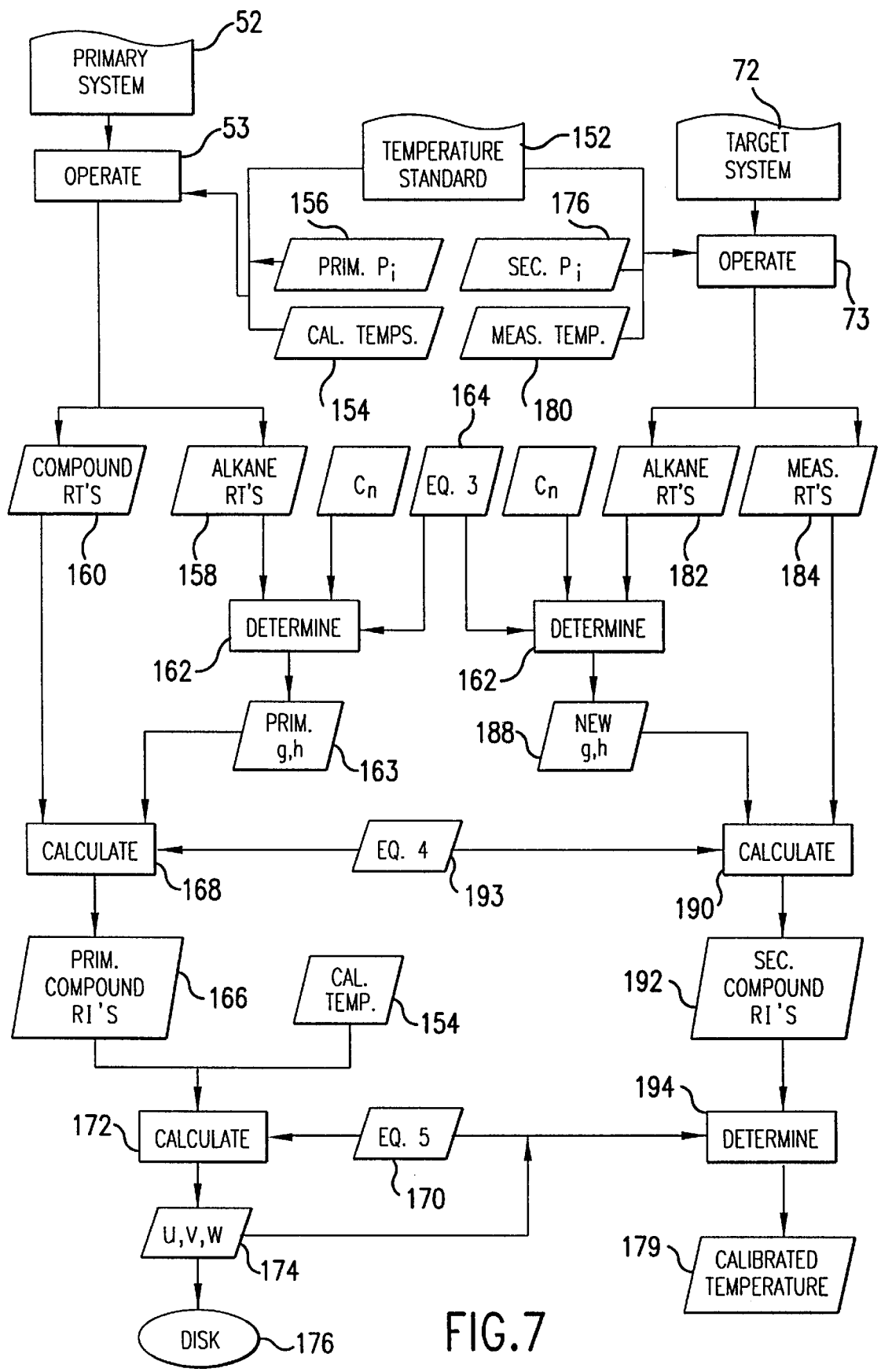
FIG. 7 is a flow chart of a method and a means for calibrating temperature of the column of the system of FIG. 1.

Preliminary retention indices 252 are calculated 168 with Eq. 4 (193) (in the same manner as for the temperature calibration with reference to FIG. 7) and, similarly, secondary validation retention indices 258 are calculated 190. The primary indices are adjusted 254 to the secondary temperature 74 with Eq. 5 (170) to effect primary validation retention indices 256.

The differences 260 between the primary and secondary validation indices are calculated 262. The test for validation 80 is whether all of the differences are within predefined limits; if so, procedures are continued from the validation 80 with respect to FIG. 3 or, if not, the procedures are stopped to investigate and fix 82 the problem.

It is intended, as an aspect of this invention, that the foregoing validation technique may also be used directly for validating a chromatographic system, independently of any standardizing.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A method of standardizing a target chromatographic system with a primary chromatographic system, each system including carrier means for passing a fluid carrier through the column, injection means for injecting a pulse of sample into the carrier to effect a mixture passing through the column subject to characteristic retention times for constituents of the sample, detector means receptive of the mixture for effecting signals representative of the retention times, and processing means receptive of the signals for presenting corresponding retention indicators, wherein each system has system parameters and operating parameters, the operating parameters comprising a first parameter having selectable first programming and a second parameter having selectable second programming, each programming being with respect to time, and the retention times being related to the system parameters and the operating parameters by a mathematical function having function parameters including thermodynamic constants associated with interactions of the constituents with the column; the method comprising steps of:

operating the primary chromatographic system with a standard sample, a selected primary second program for the second parameter, and a plurality of selected primary first programs for the first parameter, so as to generate corresponding primary retention indicators;

fitting the primary retention indicators and the primary first programs to the function, with the primary second program, so as to determine thermodynamic constants whereby the function is representative of a virtual chromatographic system; and storing the thermodynamic constants for future application with the target chromatographic system.

2. The method of claim 1 wherein the retention indicators consist of retention times or retention indices.

3. The method of claim 1 wherein the first parameter is temperature of the column.

4. The method of claim 1 wherein each system is a gas chromatographic system, the fluid carrier is a gas carrier, and the second parameter is inlet pressure of the carrier to the column.

5. The method of claim 1 wherein the system parameters comprise column dimensions.

6. The method of claim 1 further comprising:

initially operating a target chromatographic system with the standard sample, substantially the primary second program, and a plurality of secondary first programs, so as to generate corresponding secondary retention indicators;

establishing effective system parameters for the target chromatographic system;

determining a secondary second program for which, with the effective system parameters, the function yields substantially the primary retention indicators for the primary first programs; and further operating the target chromatographic system with an application sample, the secondary second program and a selected first program, so as to generate at least one corresponding test retention indicator, whereby each test retention indicator is standardized to the virtual chromatographic system.

7. The method of claim 6 wherein the step of establishing effective system parameters comprises characterizing the target chromatographic system with effective system parameters for which the function yields substantially the secondary retention indicators for the primary first programs and the primary second program.

8. The method of claim 7 wherein the system parameters comprise column dimensions, and the step of characterizing comprises, for at least one specified column dimension, further steps of:

providing an initial data base defining a range of potential values of the specified column dimension;

computing theoretical retention indicators with the function for the potential values, with the secondary temperature programs, the thermodynamic constants and the primary pressure program;

computing differences between the theoretical retention indicators and the secondary retention indicators for the secondary temperature programs; and searching the differences for a minimum therein, such that the minimum establishes an effective value for the specified column dimension.

9. The method of claim 8 wherein the step of searching comprises adaptive non-parametric searching.

10. The method of claim 9 wherein the step of searching further comprises, preceding the non-parametric searching, a further step of coarse searching to select a narrowed data base for the non-parametric searching.

11. The method of claim 6 wherein the step of determining comprises further steps of:

providing an initial data base defining a range of potential values of at least one parameter for a secondary second program;

computing theoretical retention indicators with the function for the potential values, with the secondary first programs, the thermodynamic constants and the effective system parameters;

computing differences between the theoretical retention indicators and the primary retention indicators; and searching the differences for a minimum therein, such that the minimum establishes an effective value for the at least one parameter.

12. The method of claim 11 wherein the step of searching comprises adaptive non-parametric searching.

13. The method of claim 12 wherein the step of searching further comprises, preceding the non-parametric searching, a further step of coarse searching to select a narrowed data base for the non-parametric searching.

14. A method of standardizing a target chromatographic system with a primary chromatographic system, each system including a gas chromatographic column with associated column dimensions and a column inlet, carrier means for passing a gas carrier through the column, injection means for injecting a pulse of sample into the carrier to effect a mixture passing through the column subject to characteristic retention times for constituents of the sample, detector means receptive of the mixture for effecting signals representative of the retention times, and processing means receptive of the signals for presenting corresponding retention indicators, wherein the systems have operating parameters comprising temperature programs for column temperature and at least one pressure program of carrier pressure at the column inlet, each program being with respect to time, and the retention times being related to the operating parameters by a mathematical function having function parameters including column dimensions and thermodynamic constants associated with interactions of the constituents with the column; the method comprising steps of:

establishing primary column dimensions for the column of the primary chromatographic system;

operating the primary chromatographic system with a standard sample, a selected primary pressure program, and a plurality of selected primary temperature programs, so as to generate corresponding primary retention indicators;

fitting the primary retention indicators and the primary temperature programs to the function, with the primary pressure program, so as to determine thermodynamic constants whereby the function is representative of a virtual chromatographic system; and storing the thermodynamic constants for future application with a target chromatographic system.

15. The method of claim 14 wherein the retention indicators comprise retention times or retention indices.

16. The method of claim 14 wherein each temperature program consists of a fixed temperature or includes temperature ramping, and the pressure program consists of a fixed pressure or includes pressure ramping.

17. The method of claim 14 wherein the injector has a split flow with regulation of back pressure constituting the pressure at the column inlet.

18. The method of claim 14 wherein the function is in a form of Eq. 1 where $t_R$ is retention time, T is column temperature, a, b and c are thermodynamic constants, $\beta$ is phase ratio of column dimensions, and $t_0$ is a dead time having a temperature dependence in a proportionality to carrier gas viscosity having a predetermined temperature dependence.

19. The method of claim 18 wherein the step of fitting comprises further steps of:

providing a plurality of homolog standards having an established relationship between retention time and retention indicator, the relationship being in a form of Eq. 3 where $C_n$ is a homolog number identified to each homolog standard and g and h are constants potentially dependent on temperature;

operating the primary chromatographic system with the homolog standards at a selected temperature so as to generate corresponding standard retention times;

fitting the homolog numbers and the standard retention times to the relationship with a preselected trial value for the dead time to effect a statistical error factor for the fit;

iterating the previous step with incrementally changed dead times until a first value of dead time is ascertained that minimizes the error factor, whereby the first value corresponds to the selected temperature;

determining other values of dead time for the temperature programs from the proportionality to gas viscosity; and utilizing the function with the values of dead time to determine the thermodynamic constants.

20. The method of claim 14 further comprising:

initially operating the target chromatographic system with the standard sample, substantially the primary pressure program, and a plurality of secondary temperature programs, so as to generate corresponding secondary retention indicators;

establishing effective column dimensions for the column of the target chromatographic system;

determining an effective secondary pressure program for which, with the effective column dimensions, the function yields substantially the primary retention indicators for the primary temperature programs;

ascertaining a pressure program setting corresponding to the secondary pressure program from the calibration; and further operating the target chromatographic system with an application sample, the pressure program setting and a selected temperature program, so as to generate at least one corresponding test retention indicator, whereby each test retention indicator is standardized to the virtual chromatographic system.

21. The method of claim 20 wherein the pressure program setting is the secondary pressure program.

22. The method of claim 20 wherein the primary pressure program is a fixed primary pressure, the secondary pressure program is a fixed secondary pressure, and the step of ascertaining comprises utilizing the fixed pressure as a calibration point for calibrating effective pressure against pressure settings for the target system, selecting an operating pressure program, and ascertaining the pressure program setting corresponding to the operating pressure program.

23. The method of claim 20 wherein the step of establishing effective column dimensions comprises characterizing the target chromatographic system with effective column dimensions for which the function yields substantially the secondary retention indicators for the primary pressure program and the selected value sets.

24. The method of claim 23 wherein the column comprises a stationary phase having an effective phase thickness, and the column dimensions comprise the phase thickness, column length, and column radius.

25. The method of claim 24 wherein the step of characterizing comprises, for at least one specified column dimension, further steps of:

providing an initial data base defining a range of potential values of the specified column dimension;

computing theoretical retention indicators with the function for the potential values, with the secondary temperature program, the thermodynamic constants and the primary pressure program;

computing differences between the theoretical retention indicators and the secondary retention indicators for the secondary temperature programs; and searching the differences for a minimum therein, such that the minimum establishes an effective value for the specified column dimension.

26. The method of claim 25 wherein the step of searching comprises adaptive non-parametric searching.

27. The method of claim 26 wherein the step of searching further comprises, preceding the non-parametric searching, a further step of coarse searching to select a narrowed data base for the non-parametric searching.

28. The method of claim 20 wherein the step of determining comprises further steps of:

providing an initial data base defining a range of potential values of at least one secondary pressure program parameter;

computing theoretical retention indicators with the function for the potential values, with the secondary temperature program, the thermodynamic constants and the column dimension including the effective value for the specified column dimension;

computing differences between the theoretical retention indicators and the primary retention indicators; and searching the differences for a minimum therein, such that the minimum establishes effective values for the secondary pressure program parameters.

29. The method of claim 28 wherein the step of searching comprises adaptive non-parametric searching.

30. The method of claim 29 wherein the step of searching further comprises, preceding the non-parametric searching, a further step of coarse searching to select from potentially more than one minimum in the contour plot.

31. The method of claim 20 wherein, to determine column temperature of the target chromatographic system relative to that of the primary chromatographic system, the method further comprises steps of:

providing a temperature standard comprising a calibration compound having temperature dependent retention time, and a plurality of homolog standards having a homolog relationship between corresponding retention indicators and retention times;

operating the primary chromatographic system with the temperature standard, a selected primary pressure program and a plurality of selected calibration temperatures so as to generate a primary set of retention times for each calibration temperature, each primary set comprising homolog retention times for the homolog standards and a compound retention time for the calibration compound;

first utilizing the homolog relationship and the primary set of retention times for each calibration temperature to determine calibration constants for a temperature relationship relating retention indicator for the calibration compound to column temperature for the primary system;

operating the target chromatographic system with the temperature standard and a measured column temperature so as to generate a test set of retention times, the test set comprising test retention times for the homolog standards, and a test retention time for the calibration compound;

second utilizing the homolog relationship and the test set of retention times to determine a secondary retention indicator for the calibration compound; and applying the temperature relationship with the calibration constants and the secondary retention indicator to determine a calibrated temperature corresponding to the measured temperature.

32. The method of claim 31 wherein the retention indicator is in a form that is substantially independent of system parameters and operating parameters other than temperature, the homolog standards each having a predetermined retention indicator in such form.

33. The method of claim 32 wherein the retention indicator is retention index.

34. The method of claim 31 wherein:

the step of first utilizing comprises further steps of utilizing the standard retention times from the primary sets to determine primary homolog parameters for the homolog relationship, and calculating a primary retention indicator for the calibration compound from the homolog relationship, the compound retention time and the primary homolog parameters for each calibration temperature, thereby relating retention indicator for the calibration compound to column temperature for the primary system; and the step of second utilizing comprises further steps of utilizing the test retention times from the test set to redetermine homolog parameters for the homolog relationship, and calculating the secondary retention indicator from the homolog relationship, the redetermined homolog parameters and the measured retention time.

35. The method of claim 34 wherein, to validate the target chromatographic system, the method further comprises steps of:

providing a validation sample comprising selected validation constituents;

operating the primary chromatographic system with the validation sample, a selected primary pressure program, and a primary validation temperature, so as to generate corresponding primary validation retention times;

utilizing the homolog relationship, the primary homolog parameters corresponding to the primary validation temperature, and the primary retention times, to effect preliminary retention indicators;

operating the target chromatographic system with the validation sample, substantially the primary pressure program, and the measured column temperature so as to generate corresponding secondary validation retention times;

utilizing the homolog relationship, the redetermined homolog parameters corresponding to the measured column temperature, and the secondary validation retention times, to effect secondary validation retention indicators;

adjusting the preliminary retention indicators, with the temperature relationship and corresponding primary homolog parameters to a calibrated temperature corresponding to the secondary validation temperature so as to effect primary validation retention indicators;

calculating differences between corresponding primary validation retention indicators and secondary validation retention indicators; and determining whether the differences are less than a predetermined limit corresponding to whether the target chromatographic system is valid.

36. The method of claim 35 wherein the retention indicator is in a form that is substantially independent of system parameters and operating parameters other than temperature, the homolog standards each having a predetermined retention indicator in such form.

37. The method of claim 36 wherein the retention indicator is retention index.

38. A method of calibrating column temperature of a target chromatographic system relative to that of a primary chromatographic system, each system including a gas chromatographic column, carrier means for passing a gas carrier through the column, injection means for injecting a pulse of sample into the carrier to effect a mixture passing through the column subject to characteristic retention times for constituents of the sample, detector means receptive of the mixture for effecting signals representative of the retention times, and processing means receptive of the signals for processing corresponding retention times; the method comprising steps of:

providing a temperature standard comprising a calibration compound having temperature dependent retention time, and a plurality of homolog standards having a homolog relationship between corresponding retention indicators and retention times;

operating the primary chromatographic system with the temperature standard, a selected primary pressure program and a plurality of selected calibration temperatures for the column so as to generate a primary set of retention times for each calibration temperature, each primary set comprising homolog retention times for the homolog standards and a compound retention time for the calibration compound;

first utilizing the homolog relationship and the primary set of retention times for each calibration temperature to determine calibration constants for a temperature relationship relating retention indicator for the calibration compound to column temperature for the primary system;

operating the target chromatographic system with the temperature standard and a measured column temperature so as to generate a test set of retention times, the test set comprising test retention times for the homolog standards, and a test retention time for the calibration compound;

second utilizing the homolog relationship and the test set of retention times to determine a secondary retention indicator for the calibration compound; and applying the temperature relationship with the calibration constants and the secondary retention indicator to determine a calibrated temperature corresponding to the measured temperature.

39. The method of claim 38 wherein the retention indicator is in a form that is substantially independent of system parameters and operating parameters other than temperature, the homolog standards each having a predetermined retention indicator in such form.

40. The method of claim 39 wherein the retention indicator is retention index.

41. The method of claim 38 wherein:

the step of first utilizing comprises further steps of utilizing the standard retention times from the primary sets to determine primary homolog parameters for the homolog relationship, and calculating a primary retention indicator for the calibration compound from the homolog relationship, the compound retention time and the primary homolog parameters for each calibration temperature, thereby relating retention indicator for the calibration compound to column temperature for the primary system; and the step of second utilizing comprises further steps of utilizing the test retention times from the test set to redetermine homolog parameters for the homolog relationship, and calculating the secondary retention indicator from the homolog relationship, the redetermined homolog parameters and the measured retention time.

42. The method of claim 41 wherein, to validate the target chromatographic system, the method further comprises steps of:

providing a validation sample comprising selected validation constituents;

operating the primary chromatographic system with the validation sample, a selected primary pressure program, and a primary validation temperature, so as to generate corresponding primary validation retention times;

utilizing the homolog relationship, the primary homolog parameters corresponding to the primary validation temperature, and the primary retention times, to effect preliminary retention indicators;

operating the target chromatographic system with the validation sample, substantially the primary pressure program, and the measured column temperature so as to generate corresponding secondary validation retention times;

utilizing the homolog relationship, the redetermined homolog parameters corresponding to the measured column temperature, and the secondary validation retention times, to effect secondary validation retention indicators;

adjusting the preliminary retention indicators, with the temperature relationship and corresponding primary homolog parameters to a calibrated temperature corresponding to the secondary validation temperature so as to effect primary validation retention indicators;

calculating differences between corresponding primary validation retention indicators and secondary validation retention indicators; and determining whether the differences are less than a predetermined limit corresponding to whether the target chromatographic system is valid.

43. The method of claim 42 wherein the retention indicator is in a form that is substantially independent of system parameters and operating parameters other than temperature, the homolog standards each having a predetermined retention indicator in such form.

44. The method of claim 43 wherein the homolog standards are n-alkanes, and the retention indicator is retention index.

45. A method of validating a target chromatographic system by utilization of a primary chromatographic system, each system including a gas chromatographic column, carrier means for passing a gas carrier through the column, injection means for injecting a pulse of sample into the carrier to effect a mixture passing through the column subject to characteristic retention times for constituents of the sample, detector means receptive of the mixture for effecting signals representative of the retention times, and processing means receptive of the signals for processing the retention times, the target chromatographic system having a calibrated temperature relationship between its column temperature and column temperature for the primary chromatographic system; the method comprising steps of:

providing a validation standard comprising selected validation constituents, and a plurality of homolog standards having a homolog relationship between corresponding retention indicators and retention times;

operating the primary chromatographic system with the validation standard, a selected primary pressure program, and a primary validation temperature for the column, so as to generate primary validation retention times for the validation constituents and homolog retention times for the homolog standards;

operating the target chromatographic system with the validation standard, substantially the primary pressure program, and the measured column temperature so as to generate secondary validation retention times for the validation constituents and test retention times for the homolog standards;

utilizing the homolog retention times to determine primary homolog parameters for the homolog relationship, and the test retention times to determine secondary homolog parameters for the homolog relationship;

utilizing the homolog relationship, the primary homolog parameters and the primary validation retention times to effect preliminary retention indicators;

utilizing the homolog relationship, the secondary homolog parameters and the secondary validation retention times to effect secondary validation retention indicators;

adjusting the preliminary retention indicators with the temperature relationship to a calibrated temperature corresponding to the secondary validation temperature so as to effect primary validation retention indicators;

calculating differences between corresponding primary validation retention indicators and secondary validation retention indicators; and determining whether the differences are less than a predetermined limit corresponding to whether the target chromatographic system is valid.

46. The method of claim 45 wherein the retention indicator is in a form that is substantially independent of system parameters and operating parameters other than temperature, the homolog standards each having a predetermined retention indicator in such form.

47. The method of claim 46 wherein the homolog standards are n-alkanes, and the retention indicator is retention index.

48. A method of determining values for one or more specified parameters for a chromatographic system, the system including carrier means for passing a fluid carrier through the column, injection means for injecting a pulse of sample into the carrier to effect a mixture passing through the column subject to characteristic retention times for constituents of the sample, detector means receptive of the mixture for effecting signals representative of the retention times, and processing means receptive of the signals for presenting corresponding retention indicators, the system having system parameters and operating parameters related to retention times by a mathematical function having function parameters including the system and operating parameters, and the function parameters having predetermined or assumed values except for the specified parameters; the method comprising steps of:

operating the system so as to generate retention indicators, providing an initial data base defining ranges of potential values of the specified parameters, computing theoretical retention indicators with the function for the potential values and the predetermined or assumed values, computing differences between the theoretical retention indicators and the secondary retention indicators, and searching the differences for a minimum therein, such that the minimum establishes an effective value for each specified parameter.

49. The method of claim 48 wherein the step of searching comprises adaptive non-parametric searching.

50. The method of claim 49 wherein the step searching further comprises, preceding the non-parametric searching, a further step of coarse searching to select a narrowed data base for the non-parametric searching.

51. The method of claim 48 wherein the system is a gas chromatographic system with a gas carrier.

52. The method of claim 51 wherein the operating parameters include program parameters of inlet pressure to the column, the system parameters include column dimensions, and the specified parameters consist of one or more of the program parameters and the column dimensions.

* * * * *